US012778544B2

(12) United States Patent
Hao et al.

(10) Patent No.: US 12,778,544 B2
(45) Date of Patent: Nov. 3, 2026

(54) INTRACARDIAC ULTRASOUND PROBE AND CATHETER SYSTEM

(71) Applicant: IMSONIC MEDICAL CHINA, INC, Kunshan (CN)

(72) Inventors: Xiaohui Hao, Kunshan (CN); Yaochun Xu, Kunshan (CN); Xiaohui Nie, Kunshan (CN)

(73) Assignee: Imsonic Medical China, Inc., Kunshan (CN)

( * ) Notice: Subject to any disclaimer, the term of this patent is extended or adjusted under 35 U.S.C. 154(b) by 22 days.

(21) Appl. No.: 18/899,911

(22) Filed: Sep. 27, 2024

(65) Prior Publication Data

US 2025/0017564 A1 Jan. 16, 2025

Related U.S. Application Data

(63) Continuation of application No. PCT/CN2022/083278, filed on Mar. 28, 2022.

(51) Int. Cl.

| | |
|---|---|
| ***A61B 8/12*** | (2006.01) |
| ***A61B 8/00*** | (2006.01) |
| ***H05K 1/11*** | (2006.01) |
| ***H05K 1/14*** | (2006.01) |

(52) U.S. Cl.
CPC ................ *A61B 8/12* (2013.01); *A61B 8/445* (2013.01); *H05K 1/118* (2013.01); *H05K 1/147* (2013.01)

(58) Field of Classification Search
None
See application file for complete search history.

(56) References Cited

U.S. PATENT DOCUMENTS

| | | | | |
|---|---|---|---|---|
| 5,467,779 | A | 11/1995 | Smith et al. | |
| 6,541,896 | B1 | 4/2003 | Piel, Jr. et al. | |
| 2004/0204650 | A1* | 10/2004 | Taylor | G01S 15/8945 600/459 |
| 2007/0157732 | A1* | 7/2007 | Lee | G10K 11/34 73/634 |

FOREIGN PATENT DOCUMENTS

| | | | | | |
|---|---|---|---|---|---|
| CN | 102908189 | B | * | 4/2015 | |
| CN | 111110281 | A | | 5/2020 | |
| CN | 113490555 | A | | 10/2021 | |
| JP | 2001093353 | A | * | 4/2001 | |
| WO | WO-2018230502 | A1 | * | 12/2018 | A61B 8/12 |

OTHER PUBLICATIONS

International Search Report issued on Nov. 28, 2022 in corresponding application No. PCT/CN2022/083278; 7 pages.

* cited by examiner

*Primary Examiner* — Michael J Carey
*Assistant Examiner* — Marjan Saboktakin
(74) *Attorney, Agent, or Firm* — Fish & Richardson P.C.

(57) ABSTRACT

An intracardiac ultrasound probe and a catheter system. An innovative design of flexible circuit boards and multi-core coaxial cables are used. The flexible circuit boards are extended in length or width, and the multi-core coaxial cables are configured to connect to the flexible circuit boards, so that a thickness and width of the flexible circuit boards soldered with the multi-core coaxial cables are within an allowable range of an inner diameter of a bendable ultrasound catheter. The multi-core coaxial cables reduce the coupling crosstalk between the array element signals, improve the electromagnetic shielding effect between wires, avoid the phenomena of reduced image detail and contrast resolution, thus facilitate a better image quality compared to prior art.

19 Claims, 5 Drawing Sheets

FIG. 9
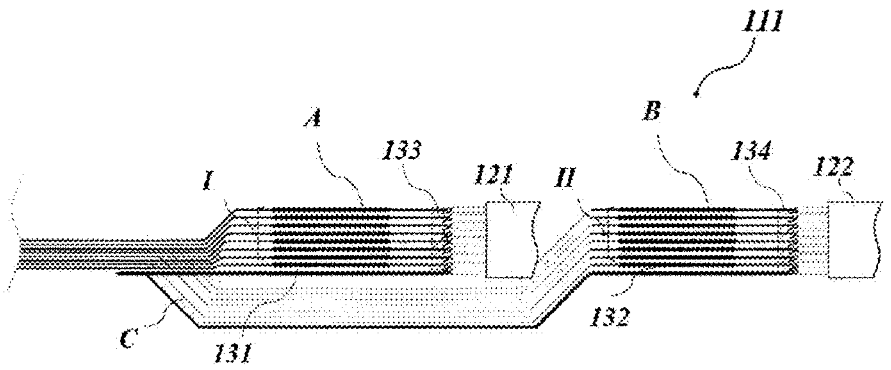
FIG. 10
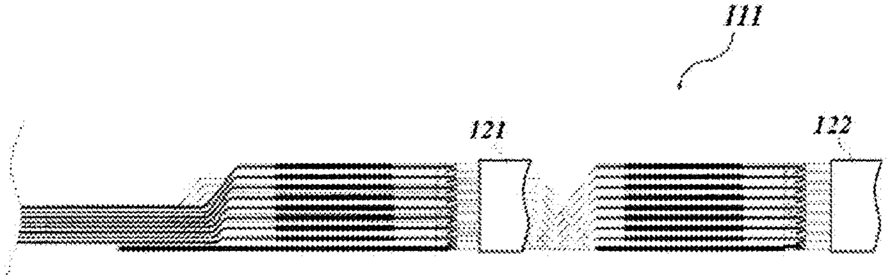
FIG. 11
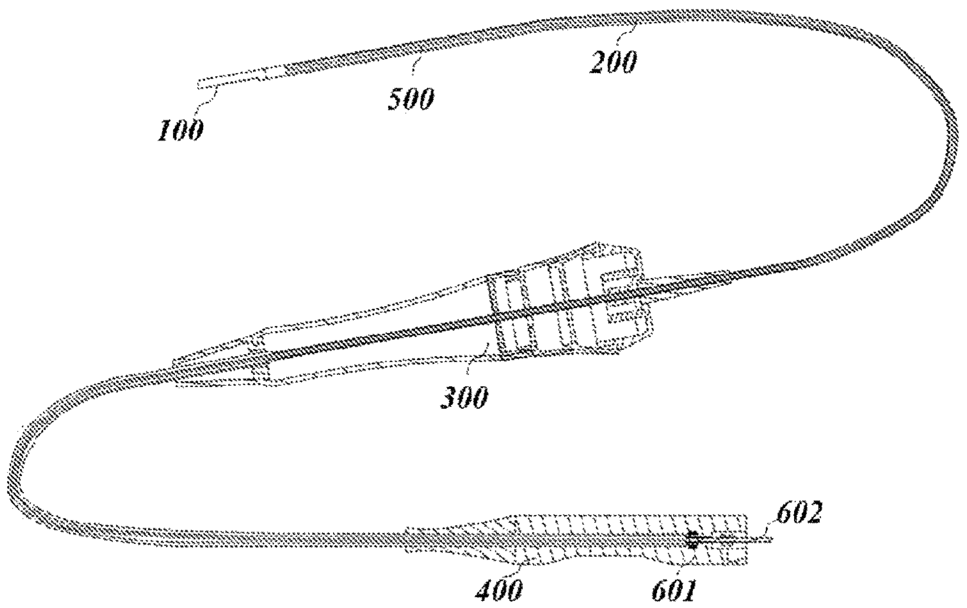
FIG. 12

INTRACARDIAC ULTRASOUND PROBE AND CATHETER SYSTEM

TECHNICAL FIELD

The present invention relates to the technical field of ultrasound detection devices, more specifically, to an intracardiac ultrasound probe and a catheter system.

BACKGROUND

Intracardiac ultrasound is a milestone advancement in cardiac imaging. In various percutaneous puncture interventions and electrophysiological examinations, the intracardiac ultrasound has gradually become an indispensable technology. This technology effectively reduces surgical risks and also improves surgical treatment effects.

In an interventional surgery, the intracardiac ultrasound can provide a real-time evaluation of a cardiac anatomical structure for a surgeon and guide operations at different anatomical levels. Compared with traditional esophageal ultrasound, the intracardiac ultrasound can be implemented in a conscious and calm state of a patient without the need for airway intubation, thereby avoiding esophageal damage. This technology shortens the surgery time, and also can reduce the radiation exposure of the surgeon and the patient during the surgery with improved surgical treatment effects. The application of the intracardiac ultrasound also plays an early warning role in the occurrence of complications such as thrombosis. In most electrophysiological surgeries, the intracardiac ultrasound is widely used and has become an essential tool for an atrial fibrillation ablation surgery. The intracardiac ultrasound is also widely used in the ablation of atrial flutter and other atrial abnormalities. For example, it can assist in the isolation and ablation of the isthmus in a typical patient with atrial flutter. The intracardiac ultrasound can achieve real-time visualization of some specific anatomical structures in the ablation of ventricular arrhythmia, and can continuously evaluate the contact between the ablation catheter and tissues, thereby improving the ablation efficiency and reducing surgical risks. This technology also provides great assistance in fields such as myocardial biopsy and early identification of surgical complications.

Due to the need to establish a channel to enable an intracardiac ultrasound probe to enter a body through femoral venous puncture, an outer diameter of the intracardiac ultrasound probe is usually 8 F to 12 F, F is an abbreviation for French, an inner diameter is generally within 2.8 mm. The catheter has a length of 90 cm toward the distal end to allow a length of 70 cm to 80 cm tube entering the human body. The distal end of the catheter is generally provided with a 64 elements ultrasound phased array. According to the requirements for intracardiac imaging, the acoustic head needs to be able to bend in 4 directions, and the maximum bending angle is generally up to 160 degrees. The intracardiac ultrasound probe is a disposable device, and an additional intermediate connector is required between the intracardiac ultrasound probe and the transducer connecting port of an imaging system. In addition, the intracardiac ultrasound catheter also needs to meet the EMC and electrical safety regulations for medical devices. These requirements make the wiring and connection between the intracardiac ultrasound transducer and the imaging system as well as the intermediate connecting parts very crucial.

In the prior art, an intracardiac ultrasound catheter typically uses flexible circuit boards to connect ultrasound transducer element electrodes to the intermediate connector. However, flexible circuit boards with a length of 90 cm to 120 cm are expensive, and the implementation of electromagnetic shielding and manufacturing processes for long flexible circuit boards are relatively complex. Usually, flexible circuit boards stacked together are wrapped with copper foil, and a thickness of the copper foil seriously affects the shielding effect on electromagnetic radiation. There are often various strong electromagnetic radiation devices in operating rooms of hospitals, due to insufficient thickness of single-layer copper foil, the shielding is inadequate, which often causes strong interference to array element signals. However, the use of too thick copper foil may prevent the insertion into the catheter due to the limitation of the inner diameter of the catheter. In real practice, the copper foil is generally thinner, typically a plastic membrane with thin copper coating and signals are susceptible to interference, resulting in relatively strong environmental electromagnetic interference noise in images. Furthermore, due to the limitation of the inner diameter of the intracardiac catheter, the width of the flexible circuit board is usually less than 2 mm. At least four long flexible circuit boards are used to connect 64 ultrasound array elements. Each long flexible circuit board needs to accommodate at least 16 signal wires in a space of 2 mm or less, and the flexible circuit board cannot have multiple layers of circuits due to the requirement for flexibility. Therefore, a distance between the signal wires on the flexible circuit board is usually very small, and long-distance transmission greater than 90 cm causes very serious crosstalk between signals, resulting in reduced image resolution and poor contrast. In addition, it is difficult to add a shielding ground layer to the flexible circuit board due to the requirement for flexibility. As mentioned above, the flexible circuit boards are usually stacked together due to size limitation. Therefore, transmission signals on a plurality of flexible circuit boards stacked together are prone to interactive interference between signals, which further causes a decrease in imaging detail resolution and contrast resolution. Moreover, the expensive cost of the long flexible circuit boards often discourages many patients.

SUMMARY

Aiming at the problems such as reduced image resolution, poor contrast, degraded image quality, insufficient electromagnetic shielding, and excessive electromagnetic radiation caused by interactive interference between array element signals of an intracardiac ultrasound probe in the prior art, and a current situation of high manufacturing cost of the intracardiac ultrasound probe in the prior art, the present invention provides an intracardiac ultrasound probe and a catheter system. An innovative design of flexible circuit boards is used, and flexible circuit boards are extended for wire connection. Moreover, instead of the long flexible circuit boards configured to connect the ultrasound transducer to the system, double-layer shielded coaxial cables are used in this innovation, they can greatly reduce the coupling crosstalk between signals, improve the electromagnetic shielding effect between wires, and result in good imaging quality, with a lower cost, and simpler manufacturing processes, thus are good for extensive use.

The objectives of the present invention are achieved through the following technical solutions.

The ultrasound probe of the present invention is suitable for ultrasound detection, especially for intracardiac ultrasound detection. It resolves the problem of serious interactive interference among a large number of wiring signals with insufficient signal shielding and too small distance among each other for long-distance transmission inside a jammed inner space in the intracardiac ultrasound catheter, provides a better electromagnetic shielding effect. As a result, the presented intracardiac ultrasound catheter has a greatly improved image quality lower cost, and is easier to manufacture, thereby achieving the objectives of reducing the cost and improving the quality.

According to a first aspect, the present invention discloses an intracardiac ultrasound probe, including an acoustic head unit and a flexible circuit board unit, where the flexible circuit board unit includes a plurality of flexible circuit boards; and the flexible circuit board includes a first connecting part laid on the acoustic head unit, a middle connecting part for wiring out signals, and a second connecting part provided with solder pads, and a length or width of the second connecting part of the flexible circuit board is extended according to the distribution of the solder pads.

Further, the width of the second connecting part is extended to twice or more of a width of the first connecting part or the middle connecting part, the solder pads are divided into two parallel groups, and each group includes signal solder pads for soldering signal wires and ground solder pads for grounding; and a gap is reserved between the two groups, the gap is used for folding of the flexible circuit board after the flexible circuit board is soldered with cable wires through the solder pads, and two sides of the folded flexible circuit board without soldered cable wires are attached together. The flexible circuit board with soldered wires is folded reversely, so that the sides without soldered wires are attached together back to back, and two sides with soldered wires face outward oppositely. The thickness and width of the stacked folded wires and solder pads with soldered wires meet the requirement of an inner size of the intracardiac ultrasound catheter.

Further, the length of the second connecting part is extended, the solder pads are divided into two groups in parallel in a length direction, and each group includes signal solder pads for soldering signal wires and ground solder pads for grounding; and a gap is reserved between the two groups, the two groups are connected through the extended connecting part, the extended connecting part is not provided with solder pads and is used for folding of the flexible circuit board after the flexible circuit board is soldered with wires, and the folded extended connecting part partially covers the signal solder pad. The solder pads are arranged side by side. After the wires are soldered to the flexible circuit board, since that only one group of wires and solder pads are provided at each position, the thickness and width thereof can easily meet the requirement of an inner diameter of the intracardiac ultrasound catheter. Both parallel arrangement and side-by-side arrangement avoid the situation of thickness increase caused by the superimposition and stacking of a plurality of circuit boards after wire soldering, so that the soldered part can be easily inserted into the catheter.

Further, in an implementation, a tail end of the flexible circuit board is provided with common ground solder pads which are perpendicular to the signal solder pad and the ground solder pad and spaced at certain intervals, and are configured for common grounding of multi-core coaxial wire shielding layers; and two groups of common ground solder pads are provided, and a gap is formed between the two groups of common ground solder pads for folding after the wire shielding layers are soldered.

Electrodes of a plurality of array elements of the acoustic head unit of the intracardiac ultrasound probe are led out through multiple flexible circuit boards, and each flexible circuit board is unfolded after being led out to facilitate soldering. After each flexible circuit board and coaxial cables are soldered and correctly grounded, the soldered flexible circuit board and the connected wires will be folded; or in the design of extending in a length direction, the extended connecting part for wiring in the flexible circuit board will be folded after soldering; and finally, a thickness and width of the folded flexible circuit board and the multi-core coaxial cables are within an allowable range of an inner diameter of a bendable catheter, and then, the multi-core coaxial cables will pass through the catheter.

The wiring method of the present invention considers the ease of soldering under the restriction of an extremely small inner diameter and the requirement for the soldered plate to pass through the inner diameter of the catheter after shielding, and provides excellent shielding for electromagnetic compatibility requirements and electromagnetic radiation requirements of the connecting wires and the acoustic head unit in the ultrasound probe.

Further, the length of each flexible circuit board in the flexible circuit board unit is different, and a length difference region between the flexible circuit boards is configured for arrangement of solder pads and accommodation of wires. The length of each flexible circuit board is different, and sufficient positions for soldering signal wires and ground shielding wires are staggered at the second connecting part of the flexible circuit board, thereby avoiding the situation that soldered positions of multiple strands of wires are overlapped and crowded beyond the inner diameter of the cardiac catheter.

Further, the signal wire is a multi-core coaxial cable. The present invention directly uses the multi-core coaxial cable instead of the flexible circuit boards to connect the leading-out circuit board of the acoustic head unit to an intermediate connector that connected to the system end, thereby greatly reducing the cost.

Further, a metal shielding mesh is arranged outside each coaxial cable, and a metal shielding layer is arranged at the outermost layer of all coaxial cables after combination. The multi-core coaxial cable has excellent electromagnetic shielding performance, and each wire in the coaxial cable has a metal shielding mesh. After the metal shielding mesh is grounded, the Faraday cage effect is formed to shield the electromagnetic signals generated by the wires inside the coaxial cable. A metal shielding layer is arranged at the outermost layer of all coaxial cables after combination. After the metal shielding layer is grounded through a system housing, the Faraday cage effect is also formed so as to form double-layer shielding together with the Faraday cage formed by the metal shielding mesh of each wire. The double-layer shielding minimizes the electromagnetic radiation of the cable to the outside and the electromagnetic interference of the outside to the cable wires. Furthermore, any two wires in the multi-core coaxial cable are separated by at least two metal shielding layers or Faraday cages, resulting in very small mutual signal crosstalk.

Further, the ground solder pad is configured to connect to the signal wire or the shielding layer. The ground solder pad includes ground soldering with a ground signal wire, and also includes ground soldering with a coaxial cable shielding layer.

In the innovative design of the present invention, the flexible circuit boards are extended, the multi-core coaxial cable with good shielding are used, and a unique wiring method and a unique connecting manner applied, thereby reducing the manufacturing cost of a disposable intracardiac ultrasound probe, improving the problems in image quality and electromagnetic shielding caused by interactive interference between signals, and improving the imaging quality.

According to a second aspect, the present invention discloses a catheter system, including the ultrasound probe, an ultrasound catheter, a control handle, and an intermediate connector, where one end of the ultrasound catheter is connected to the ultrasound probe, and inside the catheter accommodates the flexible circuit board unit of the ultrasound probe and connector wires connected to the flexible circuit board unit, the other end of the ultrasound catheter is connected to the control handle, the other end of the control handle is connected to the intermediate connector, and the intermediate connector is configured to connect to the system end. The ultrasound element connecting wires in the present invention are soldered to a circuit board with EMC shielding, and the circuit board is plugged into a gold finger slot socket from the system end through a gold finger, thereby completing the connection between the probe and the system.

Further, the connector wires first pass through a magnetic ring through the intermediate connector and are then connected to the system end. The magnetic ring can inhibit electromagnetic radiation of wires.

Further, both front and back sides of the circuit board at the system end are provided with metal shielding covers. The metal shielding cover is configured to shield electromagnetic radiation of signals and isolate external electromagnetic interference.

Further, the flexible circuit board unit and a connector are externally sleeved with a first layer of heat shrinkable tube, the first layer of heat shrinkable tube is further wrapped with a metal shielding layer or a metal mesh, and the metal shielding layer or the metal mesh is connected to a shielding cover at an outer layer of the connector through wires.

Further, a second layer of heat shrinkable tube is arranged outside the metal shielding layer or the metal mesh.

In the above two implementations, after a plurality of flexible circuit boards and a plurality of groups of multi-core coaxial cables are soldered and folded, the soldered part of four flexible circuit boards and coaxial cables is sleeved with a heat shrinkable tube, such as a Teflon heat shrinkable tube, and the heat shrinkable tube covers the soldered coaxial cable part from the tail end of the acoustic head of the ultrasound probe to the extreme end of the flexible circuit board. After heat shrinkage of the heat shrinkable tube is completed, the outer layer of the heat shrinkable tube is wrapped with a copper shielding layer or a copper mesh, and the copper shielding layer or the copper mesh is connected to the shielding layer at the outermost layer of the multi-core coaxial cable through wires. In another implementation, the outside of the shielding layer is also sleeved with a layer of Teflon heat shrinkable tube to ensure that the soldering between the multi-core coaxial wires and the flexible circuit boards is sufficiently resilient and strong to withstand the stress of multiple bending of the catheter.

Further, the control handle controls the ultrasound probe tip to bend in four spatially orthogonal directions through metal or nylon guide wires embedded in the ultrasound catheter.

Further, the ultrasound catheter is connected to the ultrasound probe by sleeving a cylindrical connecting unit of the ultrasound probe, and a diameter of the cylindrical connecting unit is smaller than a diameter of a housing of the acoustic head unit of the ultrasound probe.

3. Beneficial Effects

Compared with the prior art, the present invention has the following advantages:

(1) In the present invention, a sufficient space is provided for solder pads of electrode lead wires by extending the second connecting part of the flexible circuit board in both the width direction and length direction, so that the soldering of coaxial cables becomes easier. Furthermore, the flexible circuit board and the wires in the coaxial cable group are soldered and then folded, so that the combined width and thickness of the flexible circuit board and the wires are within the allowable range of the inner diameter of the bendable catheter, and it is convenient to place the soldered combination into the catheter.

(2) In the present invention, multi-core coaxial cables and a special coaxial cable metal shielding layer grounding technique are used to form two layers of Faraday cage protection between transmission wires for the long-distance parallel transmission signals from each array element of the ultrasound transducer to generate sufficient and effective ground wire shielding, thereby avoiding the phenomena of poor image resolution, reduced image contrast resolution and increased noise in image caused by mutual interference between signals.

(3) In the present invention, the grounded metal shielding layer at the outermost layer of the multi-core coaxial cable also protects transmission signals from interference from external electromagnetic signals in complex electromagnetic working environments, and limits electromagnetic radiation of a plurality of transmission wires to the outside during long-distance transmission.

(4) In the present invention, multi-core coaxial cables are used to connect the leading-out circuit board of the acoustic head unit to the intermediate connector connected to the system end. Compared to the use of multiple strands of flexible circuit boards with a length greater than 90 cm, the cost is reduced. For a disposable intracardiac ultrasound probe, this embodiment is lower in manufacturing cost and is suitable for extensive promotion.

BRIEF DESCRIPTION OF THE DRAWINGS

FIG. 9 is a schematic diagram of another arrangement technique of the flexible circuit boards in the ultrasound probe in the present invention;

FIG. 10 is a schematic diagram of another connection method of the flexible circuit boards and the coaxial cables in the ultrasound probe in the present invention;

FIG. 11 is a schematic diagram of folding of a flexible circuit board in the ultrasound probe in the present invention after the flexible circuit board is connected by the method described in FIG. 10;

FIG. 12 is a schematic diagram of a cross-sectional structure of an ultrasound catheter and connecting wires in the present invention;

DETAILED DESCRIPTION

The present invention is described in detail below with reference to the accompanying drawings of the specification and specific embodiments.

Embodiment 1

Figure 1:
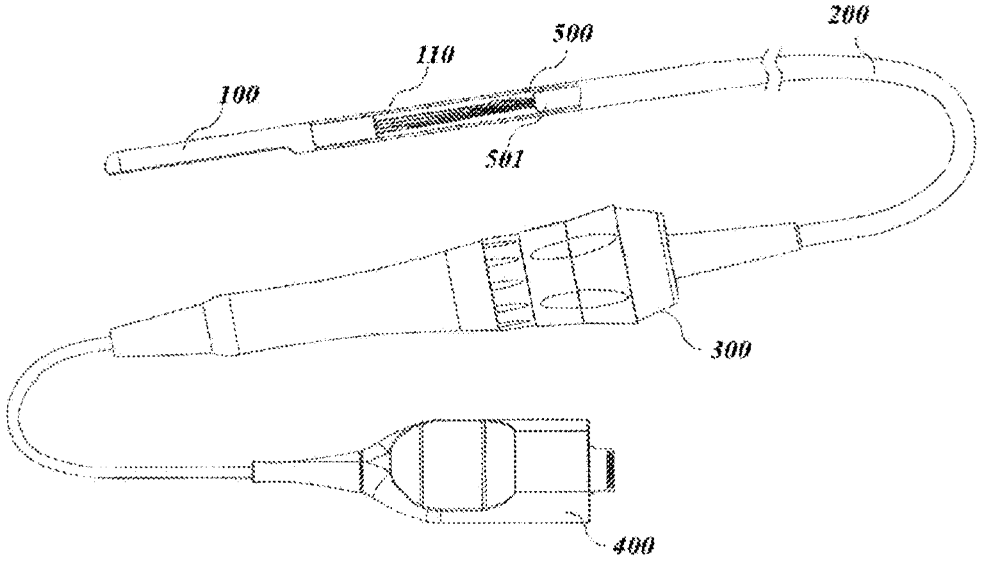
FIG. 1 is a schematic structural diagram of an ultrasound catheter system in the present invention.

This embodiment discloses a catheter system which can be used for ultrasound detection and is especially suitable for intracardiac ultrasound detection. The structure of the catheter system is shown in FIG. 1. The catheter system includes an ultrasound probe 100, an ultrasound catheter 200, a control handle 300, and an intermediate connector 400. As shown in FIG. 1, electrodes of the ultrasound probe 100 are led out through a flexible circuit board unit 110, that is, the flexible circuit board unit 110 is configured for connection of the ultrasound probe 100. The flexible circuit board unit 110 includes a plurality of flexible circuit boards, and gold fingers of each flexible circuit board are connected to a connector 500. The distal end of the ultrasound catheter 200 is connected to the ultrasound probe 100 by sleeving the flexible circuit board unit 110 and the connector 500, and the ultrasound probe 100 is provided with a bending part 501 at a certain distance from the joint between the flexible circuit board unit 110 and the connector 500. The bending part 501 serves as a turning point which allows the ultrasound probe 100 to bend freely at any angle of 0 to 160 degrees in four orthogonal directions given in space. The bending part 501 is generally arranged at a position 10 mm from the joint toward the proximal/handle end. The proximal end of the ultrasound catheter 200 is connected to the control handle 300, the other end of the control handle 300 is connected to the intermediate connector 400, and the intermediate connector 400 is configured to connect to a probe cable assembly at a system end.

The ultrasound probe 100 in this embodiment is specifically illustrated by a linear array acoustic head of a one-dimensional phased array including 64 array elements as an example. Correspondingly, the flexible circuit board unit 110 includes at least four flexible circuit boards. An outer diameter of the ultrasound catheter 200 is 8F to 12F, where F is an abbreviation for French. The control handle 300 controls the ultrasound probe 100 to freely bend in four directions by taking the bending part 501 as a turning point through metal or nylon guide wires embedded in the ultrasound catheter 200.

Figure 2:
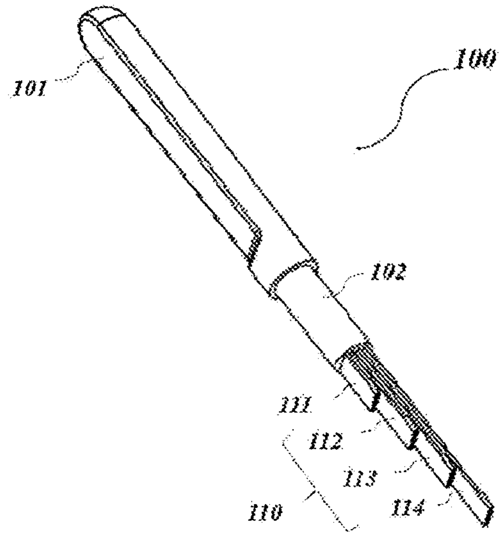
FIG. 2 is a schematic diagram of the structure and wiring of an ultrasound probe in the present invention.

A schematic diagram of the structure and wiring of the ultrasound probe 100 is shown in FIG. 2. The ultrasound probe 100 includes an acoustic head unit 101, a cylindrical connecting unit 102, and the flexible circuit board unit 110 as mentioned above. The acoustic head unit 101 includes array elements of the probe, a backing layer, a multiple matching layers, and a housing. The cylindrical connecting unit 102 is configured to solder to the ultrasound catheter 200. A diameter of the cylindrical connecting unit 102 is smaller than a diameter of the housing of the acoustic head unit 101. The ultrasound catheter 200 sleeves the soldered cylindrical connecting unit 102 of the ultrasound probe 100. In this case, the flexible circuit board unit 110 is accommodated inside the ultrasound catheter 200.

64 electrodes corresponding to 64 array elements of the acoustic head unit 101 are led out through the four flexible circuit boards of the flexible circuit board unit 110. In FIG. 2, the four flexible circuit boards are respectively a first flexible circuit board 111, a second flexible circuit board 112, a third flexible circuit board 113, and a fourth flexible circuit board 114. Each flexible circuit board is responsible for wiring out electrode signals of 16 ultrasound array elements, as well as two paths of ground signals.

It can be seen from FIG. 2 that the flexible circuit board each have different lengths, and are arranged in a stepped manner. That is, the second flexible circuit board 112 is longer than the first flexible circuit board 111, the third flexible circuit board 113 is longer than the second flexible circuit board 112, and the fourth flexible circuit board 114 is longer than the third flexible circuit board 113. The difference in length between the flexible circuit boards is exactly a distance required for the arrangement of signal solder pads and ground solder pads of shielding layers, as well as for soldering with multi-core coaxial cables.

Figure 3:
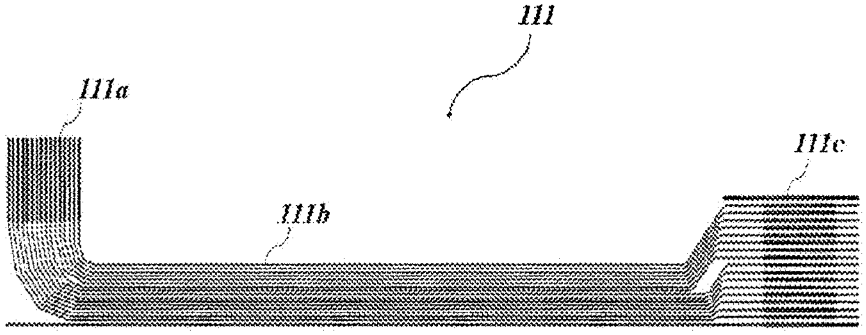
FIG. 3 is a schematic structural diagram of a flexible circuit board in the ultrasound probe in the present invention.

For the convenience of description, a flexible circuit board is simply divided into three parts. As shown in FIG. 3, taking the first flexible circuit board 111 as an example, a first connecting part 111*a* of the first flexible circuit board 111 is laid between the array elements of the acoustic head unit 101 and the matching layer, and passes through a middle connecting part 111*b* of the first flexible circuit board 111, and a second connecting part 111*c* of the first flexible circuit board 111 is configured to solder to wires. For more intuitive description, the first connecting part of each of the flexible circuit boards in this embodiment is also referred to as an a-end or a front end of the flexible circuit board in the following text, and the second connecting part of each of the flexible circuit boards is also referred to as a c-end or a tail end of the flexible circuit board in the following text.

Figure 4:
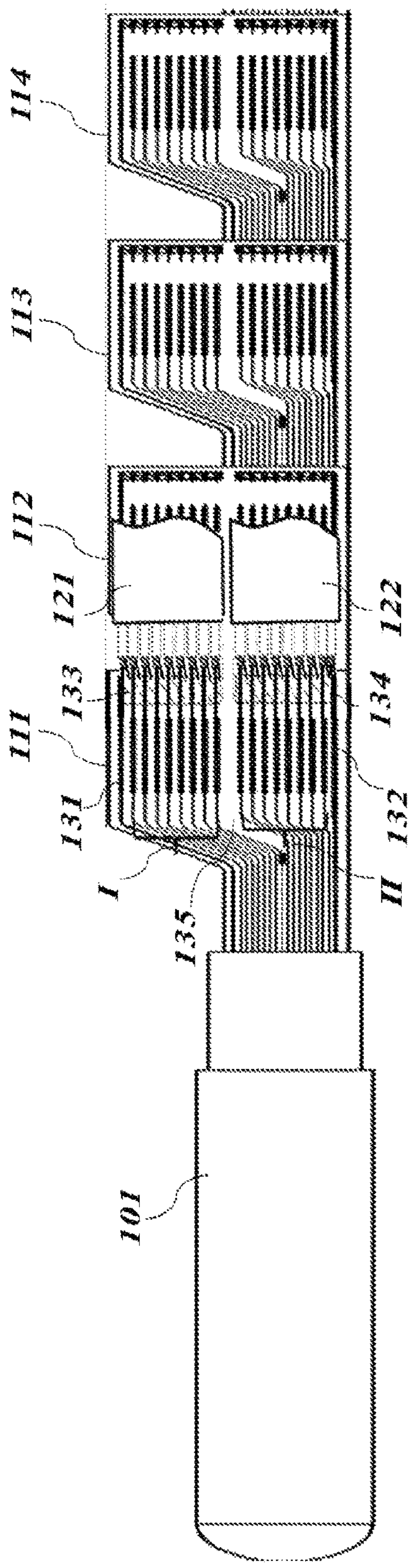
FIG. 4 is a schematic diagram of a connection method of flexible circuit boards and coaxial cables in the ultrasound probe in the present invention.

As shown in FIG. 4, the second connecting parts of the four flexible circuit boards 111, 112, 113, and 114 for connection to the wires are unfolded in a width direction to be at least twice a width of the first connecting part and the middle connecting part of the circuit board, and the unfolded second connecting part is configured for placement of up to 18 solder pads. Still taking the first flexible circuit board 111 as an example, 16 middle solder pads are divided into two groups: group I and group II, each group includes 8 solder pads, each solder pad corresponds to one signal wire, and a larger gap 135 is reserved between the two groups. An edge of the flexible circuit board is provided with two ground solder pads, namely a first ground solder pad 131 and a second ground solder pad 132. During soldering of wires, a first coaxial cable group 121 and a second coaxial cable group 122 each have nine wires, as shown in FIG. 4, 8 wires in the 9 wires of the wire group of the first coaxial cable group 121 are respectively soldered to the solder pad group I, one grounded wire is soldered to the first ground solder pad 131, and a shielding mesh of each wire and a shielding layer of the wire group are led out through the wires to a transverse third ground solder pad 133 at the tail end of the flexible circuit board and connected to the first ground solder pad 131. Similarly, 8 wires in the 9 wires of the wire group of the second coaxial cable group 122 are respectively soldered to the solder pad group II, one grounded wire is soldered to the second ground solder pad 132, and a shielding mesh of each wire and a shielding layer of the wire group are led out through the wires to a fourth ground solder pad 134 which is in transverse direction at the tail end of the flexible circuit board and connected to the second ground solder pad 132. It is noted that the third ground solder pad 133 and the fourth ground solder pad 134 are perpendicular to the solder pad group I and the solder pad group II as well as the ground solder pad 131 and the ground solder pad 132, thereby facilitating the stripping of the shielding layer of each wire in the first coaxial cable group 121 and the second coaxial cable group 122, followed by soldering and grounding. In another implementation, the third ground solder pad 133 and the fourth ground solder pad 134 are not arranged in the first flexible circuit board 111. During soldering, shielding layers of the nine wires in the first coaxial cable group 121 are stripped and directly soldered together, and then soldered to the first ground solder pad 131 to achieve the objective of shielding layer grounding; and shielding layers of the nine wires in the second coaxial cable group 122 are stripped and directly soldered together, and then soldered to the second ground solder pad 132 to achieve the objective of shielding layer grounding.

It can be seen from FIG. 4 that a gap is reserved between the transverse third ground solder pad 133 and the transverse fourth ground solder pad 134 at the tail end of the flexible circuit board. This gap is an extension of the gap 135, which is for the convenience of folding. After the two coaxial cable groups 121 and 122 each with nine wires respectively and the first flexible circuit board 111 are soldered, a gluing process is applied, then the upper part of the gap 135 of the first flexible circuit board 111 and the first coaxial cable group 121 soldered to the flexible circuit board are folded reversely, such that two sides of the second connecting part of the first flexible circuit board 111 without soldered wires are attached, and two sides soldered with the first coaxial cable group 121 and the second coaxial cable group 122 face outward, thereby avoiding the short circuit between soldering wires.

Figure 5:
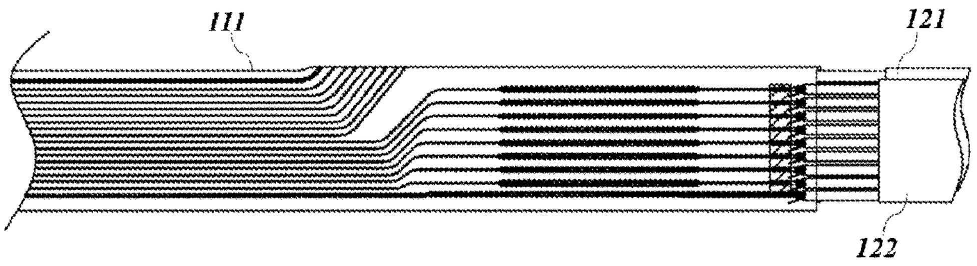
FIG. 5 is a schematic diagram of folding of a flexible circuit board in the ultrasound probe in the present invention after the flexible circuit board is connected by the method described in FIG. 4.
Figure 14:
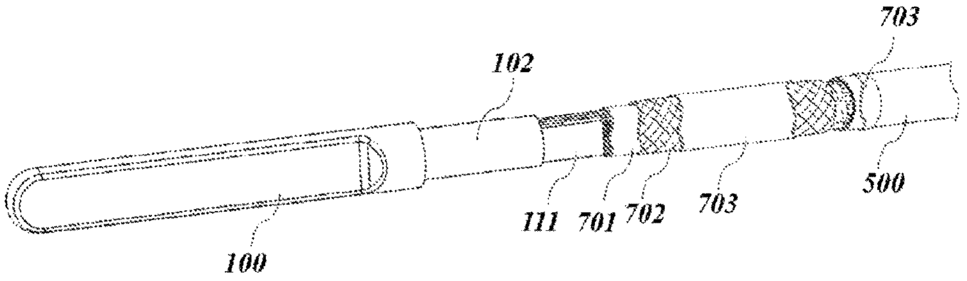
FIG. 14 is a schematic diagram of wrapping heat shrinkable tubes and shielding layers outside soldering between a flexible circuit board and a coaxial cable in the present invention.

The folded first flexible circuit board 111 is connected to the first coaxial cable group 121 and the second coaxial cable group 122 with nine coaxial cables respectively, as shown in FIG. 5. Both a width and a thickness of the superimposed folded flexible circuit boards are within an allowable range of an inner diameter of the bendable ultrasound catheter 200. The four folded flexible circuit boards soldered with coaxial cables are sleeved with a heat shrinkable tube, such as a Teflon heat shrinkable tube as an example in this embodiment. As shown in FIG. 14, a first layer of heat shrinkable tube 701 covers from the cylindrical connecting unit 102 at the tail end of the ultrasound probe 100 to the coaxial cable soldered with the fourth flexible circuit board 114 at the extreme end of the flexible circuit board unit 110. After heat shrinkage of the first layer of heat shrinkable tube 701 is completed, the outside of the first layer of heat shrinkable tube 701 will be wrapped with a metal shielding mesh 702 or a metal shielding layer, and the metal shielding mesh 702 is connected to the shielding cover at the outermost layer of the multi-core coaxial cable which is defined as a connecting part 500 through wires. The combination is easier to be inserted into the bendable ultrasound catheter 200.

As an improvement of this embodiment, the metal shielding mesh 702 outside the heat shrinkable tube is further sleeved with a second heat shrinkable tube 703, thereby ensuring that the soldering between the multi-core coaxial cables and the flexible circuit board unit 110 is sufficiently resilient and strong to withstand the stress of multiple bending of the catheter.

Figure 6:
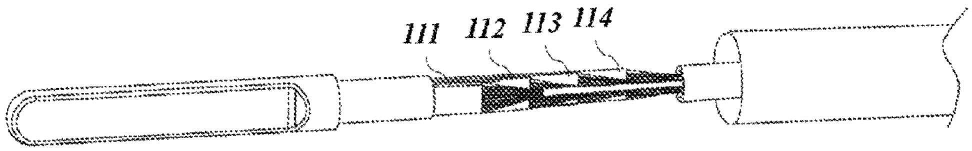
FIG. 6 is a schematic diagram of wiring out acoustic head signals after the flexible circuit boards and a plurality of coaxial cables in the ultrasound probe in the present invention are soldered and folded.

As shown in FIG. 6, the other three flexible circuit boards 112, 113 and 114, soldered with multiple groups of coaxial cables, and ground shielding wires are folded in the same way. The four flexible circuit boards are soldered with eight groups of nine coaxial cables, and a total of 72 coaxial cables are configured to connect to the flexible circuit boards, namely a connecting end of an ultrasound detection probe. In this embodiment, the multi-core coaxial cable is used as connecting wires for connecting ultrasound probe electrodes to a system. Because the multi-core coaxial cable has excellent electromagnetic shielding performance, cross talk between signals can be avoided even in a very small space.

Figure 7:
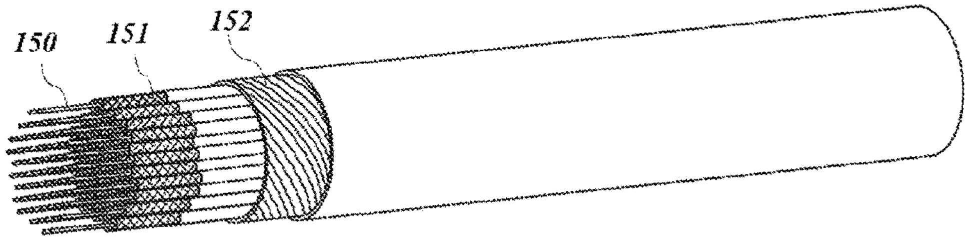
FIG. 7 is a schematic diagram of metal shielding layers of single wires and an overall metal shielding layer in a combination of a plurality of coaxial cables in the present invention.

Each coaxial cable inside the multi-core coaxial cable in this embodiment is provided with a metal shielding layer. As shown in FIG. 7, a metal shielding mesh 151 is arranged outside a wire 150 in a coaxial cable group. After the metal shielding mesh 151 is grounded, a Faraday cage effect is formed, so that an electromagnetic signal generated by the wire 150 is shielded in the coaxial cable. A metal shielding layer 152 is arranged at the outermost layer of all coaxial cables 150 after combination. After the metal shielding layer 152 is grounded through a system housing, a Faraday cage effect is also formed so as to form double-layer shielding together with the Faraday cage formed by the metal shielding mesh 151 of each wire 150. The double-layer shielding minimizes the electromagnetic radiation of the cable to the outside and the electromagnetic interference of the outside to the cable wires. Furthermore, any two wires 150 in the multi-core coaxial cable are separated by two layers of Faraday cages formed by at least two layers of metal shielding meshes 151, resulting in very small crosstalk between signals. Compared to flexible circuit boards ranging from 90 cm to 100 cm, the mutual interference between signals is much smaller. This is because the restriction of a too small internal space of the intracardiac catheter and the requirement for flexibility of the flexible circuit board make it impossible for the flexible circuit board to shield and separate the signal wires on the board with sufficient ground wires, thereby inevitably causing interactive interference between signals during long-distance transmission.

Figure 8:
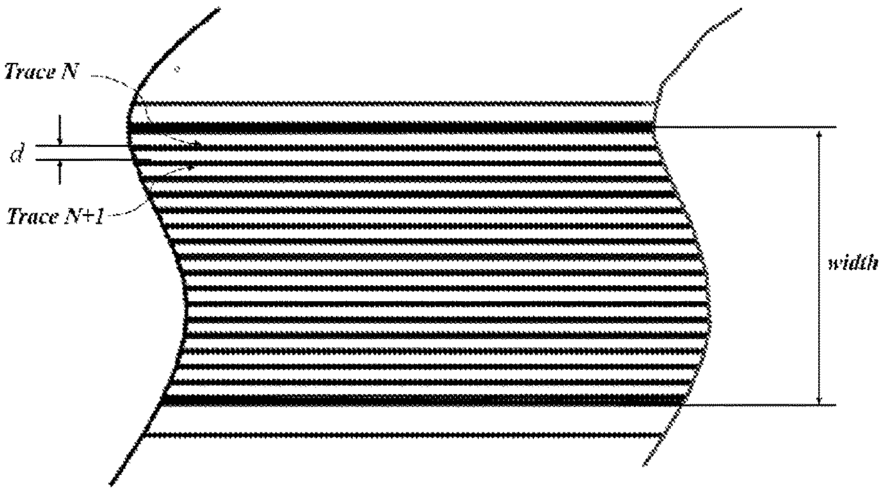
FIG. 8 is a schematic diagram of the connecting method for long distance signal transmission flex circuitry board with signal electrodes in the prior art.

FIG. 8 is a schematic diagram of a circuit board in the prior art that uses a flexible circuit board for long-distance transmission of signals acquired by acoustic head electrodes. The width of the flexible circuit board is usually about 2 mm. At least 16 signal wires are distributed on the 2 mm width, that is, a distance d between two signal transmission wires Trace N and Trace N+1 is about 0.13 mm. A length of an intracardiac ultrasound detection device is generally at least 100 cm. Adjacent signal transmission wires are very close to each other and need to transmit in parallel for 100 cm or more, and furthermore, ultrasound imaging signals are usually pulse signals, so that the electromagnetic radiation is very serious, and an electromagnetic field generated around the signal wires due to the pulse signals is very strong. The mutual interference between adjacent signal transmission wires caused by the action of the electromagnetic field between signals is directly proportional to the parallel transmission distance of the signals. At a distance of 100 cm, each signal transmission wire becomes an antenna for external transmission. In this case, the mutual interference between the signals is very serious, and adjacent transmission wires will be coupled in an antenna manner. In ultrasound imaging, this is equivalent to an increase in the pitch of array elements, which has a significant impact on the imaging quality.

For example, in beam forming, the pitch of array element has a direct impact on an angle at which a grating lobe appears during beam deflection. Assuming that λ is a wavelength of a transmitted waveform corresponding to a center frequency of the probe, an angle at which a first-order grating lobe appears in beam forming of transmission focusing can be calculated as follows:

$$GL\_ang = 180 * \sin(\sin\theta \pm \lambda / \text{pitch}) / pi,$$

$$\text{where} / \sin\theta \pm \lambda / \text{pitch} / < 1(\text{in degrees}),$$

where θ is a deflection angle of the transmitted waveform relative to a vertical direction of array element arrangement. It can be seen that the larger the pitch of equivalent array elements, the smaller the GL_ang. However, a very small first-order grating lobe angle will cause poor image focusing quality. Especially, an increase in grating lobe noise has a significant impact on a main lobe, resulting in a significant decrease in image resolution and contrast. As mentioned above, in this embodiment, the multi-core coaxial cable is used, and the metal shielding mesh of each wire of the multi-core coaxial cable and the overall metal shielding layer are grounded to form the Faraday cage effect to greatly reduce the mutual interference between array element signals in long-distance transmission, thereby ensuring a smaller effective array element pitch. A first-order grating lobe angle calculated based on this is larger, the impact on the main lobe is smaller, and image quality such as beam forming resolution and contrast resolution are better.

In this embodiment, a sufficient space is reserved for solder pads connected to wires led out from electrodes of the acoustic head unit 101 by extending and unfolding the second connecting part of the flexible circuit board in the width direction, so that the soldering of the solder pads and the coaxial cables becomes easier. Furthermore, the flexible circuit board and the wire groups of the coaxial cables are soldered together then folded back to back, so that the combined width and thickness of the flexible circuit board and the wires are within the allowable range of the inner space of the bendable catheter, and it is convenient to place the soldered combination into the catheter.

In this embodiment, the multi-core coaxial cable and a special coaxial cable metal shielding layer grounding method are used to form two layers of Faraday cage protection between transmission wires. This provides sufficient and effective ground wire shielding for signals from each array element of the probe during long-distance parallel transmission, thereby avoiding the phenomena of poor image resolution, reduced image contrast resolution and increased noise in imaging caused by mutual interference between signals. The grounded metal shielding layer 152 at the outermost layer of the multi-core coaxial cable further protects transmission signals from interference from external electromagnetic signals in complex electromagnetic working environments, and limits electromagnetic radiation of a plurality of transmission wires to the outside during long-distance transmission. In this embodiment, the use of the multi-core coaxial cables reduces the cost compared to the use of multiple strands of flexible circuit boards with a length greater than 90 cm, which is crucial for a disposable intracardiac ultrasound probe, and thus is suitable for extensive promotion.

Embodiment 2

This embodiment is basically the same as Embodiment 1, and the difference is that the flexible circuit boards and multi-core coaxial cables in this embodiment are connected by extending the flexible circuit boards in the length direction.

As shown in FIG. 9, the ultrasound probe 100 includes four flexible circuit boards, namely the first flexible circuit board 111, the second flexible circuit board 112, the third flexible circuit board 113, and the fourth flexible circuit board 114. The same as Embodiment 1, the lengths of the flexible circuit boards are arranged in a stepped manner. That is, the second flexible circuit board 112 is longer than the first flexible circuit board 111, the third flexible circuit board 113 is longer than the second flexible circuit board 112, and the fourth flexible circuit board 114 is longer than the third flexible circuit board 113.

A connected part of a front end of the flexible circuit board (i.e., the a-end or first connecting part of the flexible circuit board described in Embodiment 1) and the matching layer of the ultrasound probe 100 is the same as that in Embodiment 1. Different from Embodiment 1, in this embodiment, a tail end of the flexible circuit board (i.e., the c-end or second connecting part described in Embodiment 1) is not unfolded along the width direction for placement of 16 parallel signal wires and 2 ground wire pads, but is unfolded along the length direction as shown in FIG. 10 to divide signal wires into two groups arranged in front and back side by side.

In FIG. 10, the second connecting part of the first flexible circuit board 111 is divided into a part A and a part B, where the part A includes a pad group I with 8 parallel signal wire pads, a first ground solder pad 131 which is parallel to the signal wire pads and is arranged on an outer edge of the circuit board, and a transverse third ground solder pads 133 which are perpendicular to the solder pad group I and the first ground solder pad 131 and are spaced at certain intervals to connect to the coaxial cable shielding layer; and the part B at the tail end also includes a pad group II with 8 parallel signal wire pads, a second ground solder pad 132 which is parallel to the signal wire pads and is arranged on a peripheral edge, and a transverse fourth ground solder pads 134 which are perpendicular to the solder pad group II and the second ground solder pad 132 and are spaced at smaller intervals for grounding connection with the coaxial cable shielding layer. The part A is located near the acoustic head unit 101, namely in a relatively front position. The part B is located at the tail end of the flexible circuit board 111. There is a certain distance between the part A and the part B. As shown in FIG. 10, the signal wires and ground wires from the acoustic head unit 101 to the part B are turned at a certain distance in front of the signal wire pads in the part A, and reach the part B through an extended and widened part C of the first flexible circuit board 111.

In this embodiment, the part A and the part B are respectively connected to a group of 9 coaxial cables through soldering. When the first coaxial cable group 121 composed of nine coaxial cables is soldered to the first flexible circuit board 111, as shown in FIG. 10, eight wires of the nine wires are respectively soldered to the solder pad group I, one grounding wire is soldered to the first ground solder pad 131, and the shielding layer of each coaxial wire is led out to the transverse third ground solder pad 133 at the tail end of the part A in the first flexible circuit board 111 through a wire and connected to the first ground solder pad 131; and similarly, eight signal wires of the nine wires in the second coaxial cable group 122 composed of nine coaxial cables are respectively soldered to the signal wire solder pad group II in the part B at the tail end in the first flexible circuit board 111, one grounding wire is soldered to the second ground solder pad 132, and the shielding layer of each coaxial wire is led out to the transverse fourth ground solder pad 134 at the tail end through a wire and connected to the second ground solder pad 132. In another implementation, the transverse third ground solder pad 133 at the tail end of the part A and the transverse fourth ground solder pad 134 at the tail end of the part B are not arranged on the part A and part B of the flexible circuit board 111, and the shielding layer of each of the wires in the first coaxial cable group 121 and the second coaxial cable group 122 is soldered together through wires and then connected to the first ground solder pad 131 and the second ground solder pad 132. After the two coaxial cable groups 121 and 122 with nine coaxial cables respectively and the part A and part B of the first flexible circuit board 111 are soldered, a gluing process applied, the part C that is expanded and widened from the part A and connected to the part B is folded. The combination of the folded first flexible circuit board 111 and the two coaxial cable groups 121 and 122 with nine coaxial cables respectively is shown in FIG. 11. The width and thickness of the combination fully meets the requirement for inserting the combination into the inner space of the intracardiac ultrasound catheter. After being wrapped with a heat shrinkable tube and copper foil for shielding, the combination can be conveniently inserted into the bendable ultrasound catheter 200. The other three flexible circuit boards 112, 113 and 114 and multi-core coaxial cables are soldered and folded in the same way. After the four flexible circuit boards and the coaxial cables are soldered, the part from the cylindrical connecting unit 102 at the tail end of the ultrasound probe 100 to the fourth flexible circuit board 114 at the extreme end of the flexible circuit board unit 110 is sleeved with the heat shrinkable tube 701 as a first layer, shown in FIG. 14. After heat shrinkage of the first layer of heat shrinkable tube 701 is completed, the outside of the heat shrinkable tube 701 will be wrapped with metal shielding mesh 702 or the metal shielding layer, and the metal shielding mesh 702 is connected to the shielding cover at the outermost layer of the multi-core coaxial cable as a connecting part 500 through wires to form grounding.

As an improvement of this embodiment, the outside of the metal shielding mesh 702 is further sleeved with a layer of second heat shrinkable tube 703, thereby ensuring that the soldering between the multi-core coaxial wires and the flexible circuit board unit 110 is sufficiently resilient and strong to withstand the stress of multiple bending of the catheter. On the basis of the beneficial effects of the connection mode in Embodiment 1, in this embodiment, the flexible circuit boards are extended according to lengths, 18 solder pads for soldering of 16 signal wires and 2 ground wires, are divided into two rows placed in front and back, and a sufficient space is provided between the solder pads of the signal wires to facilitate the soldering of the coaxial cables and the metal shielding layer of each coaxial cable to the flexible circuit board. Furthermore, it avoids the situation that the folded two coaxial cable groups that are soldered, glued on the flex circuitry board to be too thick that may exceed the inner diameter of the catheter, as a result, the connecting joint between the wire and the circuit board is easier to pass through the catheter, thereby facilitating the manufacturing and installation.

Embodiment 3

On the basis of Embodiment 1 and Embodiment 2, this embodiment further discloses an intracardiac ultrasound detection device.

As shown in FIG. 12, the connector 500 connected to the flexible circuit board unit 110 of the ultrasound probe 100 passes through the bendable ultrasound catheter 200 and the bent control handle 300, and then enters the intermediate connector 400, where the connector 500 includes eight coaxial cable groups each with 9 coaxial cables respectively (72 wires in total). At the tail end of the wire, the wire first passes through a magnetic ring 601 and is then connected to a gold finger circuit board 602 of the intermediate connector connected to the system end, thereby forming a complete intracardiac ultrasound catheter probe combination. The magnetic ring 601 is arranged to inhibit the electromagnetic radiation of the connector 500 to ensure the integrity and fidelity of signals. The gold finger circuit board 602 is provided with a dedicated tuning circuit for impedance matching. Both front and back sides of the gold finger circuit board 602 are covered with metal shielding covers for shielding the electromagnetic radiation of signals and isolating the external electromagnetic interference.

Figure 13:
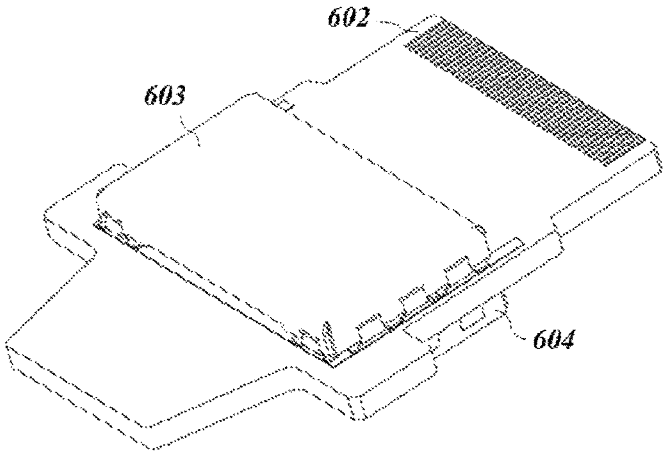
FIG. 13 is a schematic diagram of a gold finger circuit board and metal shielding covers in the present invention.

FIG. 13 is a schematic diagram of the gold finger circuit board 602 and the metal shielding covers in this embodiment, including a first shielding cover 603 arranged on the front side of the gold finger circuit board 602, and a second shielding cover 604 arranged on the back side of the gold finger circuit board 602. When the gold finger circuit board 602 is connected to the connector at the system end, the ultrasound catheter in this embodiment can be used for imaging.

The intracardiac ultrasound probe in the present invention is a disposable ultrasound probe. After use, the entire probe is discarded. The structural design and connection method of the present invention greatly reduce the electromagnetic radiation and mutual electromagnetic field coupling interference between long-distance transmission wires for the array element signal transmission, improve the detail and contrast resolution of imaging, maximize the easiness of processes such as wire soldering and catheter insertion while improving the imaging performance, provide a more reliable electromagnetic shielding effect than the prior art, and avoid excessive electromagnetic radiation of the probe or interference from external electromagnetic signals. Furthermore, in the present invention, the coaxial cables are used instead of flexible circuit boards to greatly reduce the cost, so that the disposable probe can be applied more conveniently.

The above schematically describes the present invention and implementations thereof, and the description is not restrictive. The present invention can be implemented in other specific forms without departing from the spirit or basic features of the present invention. The implementation shown in the accompanying drawings is only one of the implementations of the present invention, and the actual structure is not limited to this. Any reference numerals in the claims should not limit the claims involved. Therefore, if those of ordinary skill in the art are inspired, without departing from the inventive concept of the present invention, any structure and embodiment similar to those in the technical solution, designed without creativity, shall fall within the protection scope of the present invention. In addition, the term "include" does not exclude other elements or steps, and the term "a\an" before an element does not exclude the inclusion of "a plurality of" the elements. A plurality of elements stated in the product claims may also be implemented by one element through software or hardware. The terms such as "first" and "second" are used for representing names and do not represent any specific order.

What is claimed is:

1. An intracardiac ultrasound probe, comprising:

a multielement acoustic head unit, a flexible circuit board unit, and a multi-core coaxial cable, wherein the flexible circuit board unit and the multi-core coaxial cable are housed inside an ultrasound catheter, wherein the flexible circuit board unit comprises a plurality of flexible circuit boards, wherein each flexible circuit board of the plurality of flexible circuit boards houses a plurality of signal traces for a corresponding plurality of elements of the multielement acoustic head unit, and each flexible circuit board comprises:

a first distal connecting part laid on the multielement acoustic head unit, a second proximal connecting part provided with solder pads, and an intermediate connecting part disposed between the first distal connecting part and the second proximal connecting part for wiring out element signals from the multielement acoustic head unit, wherein the second proximal connecting part is extended in a width direction to be at least twice a width of the intermediate connecting part, the plurality of signal traces are split into two groups in which adjacent traces are spread out with increased separation as the signal traces run distally towards the solder pads, and a gap is placed between the two groups for folding of the flexible circuit board at the second proximal connecting part when the flexible circuit board is soldered with signal wires of the multi-core coaxial cable through the solder pads; and wherein the flexible circuit boards are folded to fit inside the ultrasound catheter, wherein the flexible circuit boards are connected with the signal wires of the multi-core coaxial cable to couple the multielement acoustic head unit to an intermediate connector.

2. The intracardiac ultrasound probe according to claim 1, wherein each group of the two groups comprises signal solder pads for soldering the signal wires of the multi-core coaxial cable, and ground solder pads for grounding; and two sides of each folded flexible circuit board without soldered cable wires are attached together.

3. The intracardiac ultrasound probe according to claim 1, wherein the second proximal connecting part is extended in a length direction, the solder pads are divided into two groups in parallel in a length direction, and each group comprises signal solder pads for soldering signal wires and ground solder pads for grounding; and a gap is reserved between the two groups, the two groups are connected through the extended second proximal connecting part, the extended second proximal connecting part is not provided with solder pads and used for folding of the flexible circuit board after the flexible circuit board is soldered with wires through the solder pads, and the folded extended connecting part partially covers the signal solder pad.

4. The intracardiac ultrasound probe according to claim 3, wherein a tail end of the flexible circuit board is provided with common ground solder pads which are perpendicular to the signal solder pad and the ground solder pad and spaced at certain intervals, and are used for common grounding of multi-core coaxial wire shielding layers; and two groups of common ground solder pads are provided, and a gap is formed between the two groups of common ground solder pads for folding after the wire shielding layers are soldered.

5. The intracardiac ultrasound probe according to claim 2, wherein a length of each flexible circuit board in the flexible circuit board unit is different, and a length difference region between the flexible circuit boards is configured for arrangement of solder pads and accommodation of wires.

6. The intracardiac ultrasound probe according to claim 1, wherein a metal shielding mesh is arranged outside each coaxial cable of the multi-core coaxial cable, and a metal shielding layer is arranged at the outermost layer of all coaxial cables after combination; and the metal shielding mesh outside each coaxial cable, and the metal shielding layer at the outmost of all coaxial cables are grounded to form two faraday cages for better electromagnetic shielding.

7. The intracardiac ultrasound probe according to claim 6, wherein a ground solder pad is configured to connect to the metal shielding mesh of the multi-core coaxial cable.

8. An intracardiac ultrasound catheter system, comprising the ultrasound probe according to claim 1, an ultrasound catheter, a control handle, and the intermediate connector, wherein a distal end of the ultrasound catheter is connected to the ultrasound probe, and inside the catheter accommodates the flexible circuit board unit of the ultrasound probe that lead out the ultrasound probe array element signals, and a multicore coaxial cable to connect the element signals from the flexible circuit board unit, a proximal end of the ultrasound catheter is connected to the control handle, and the multi-core coaxial cable goes through the handle to the other end of the control handle to connect to the intermediate connector, and the intermediate connector is configured to connect to a system end.

9. The intracardiac ultrasound catheter system according to claim 8, wherein the signal wires first pass through a magnetic ring to be soldered to the intermediate connector, and the intermediate connector can then be plugged into the system end.

10. The intracardiac ultrasound catheter system according to claim 9, wherein both front and back sides of the circuit board of the intermediate connector are provided with metal shielding covers.

11. The intracardiac ultrasound catheter system according to claim 10, wherein the flexible circuit board unit and the intermediate connector are externally sleeved with a first layer of heat shrinkable tube, the first layer of heat shrinkable tube is further wrapped with a metal shielding layer or a metal mesh, and the metal shielding layer or the metal mesh is connected to a shielding cover at an outer layer of the intermediate connector through wires.

12. The intracardiac ultrasound catheter system according to claim 11, wherein a second layer of heat shrinkable tube is arranged outside the metal shielding layer or the metal mesh.

13. The intracardiac ultrasound catheter system according to claim 8, wherein the control handle controls the ultrasound probe tip to bend in four spatially orthogonal directions through metal or nylon guide wires embedded in the ultrasound catheter.

14. The intracardiac ultrasound catheter system according to claim 8, wherein the ultrasound catheter is connected to the ultrasound probe by sleeving a cylindrical connecting unit of the ultrasound probe, and a diameter of the cylindrical connecting unit is smaller than a diameter of a housing of the acoustic head unit of the ultrasound probe.

15. The intracardiac ultrasound probe according to claim 3, wherein a length of each flexible circuit board in the flexible circuit board unit is different, and a length difference region between the flexible circuit boards is configured for arrangement of solder pads and accommodation of wires.

16. An intracardiac ultrasound catheter system, comprising: the intracardiac ultrasound probe according to claim 1, the ultrasound catheter, a control handle, and an intermediate connector, wherein a distal end of the ultrasound catheter is connected to the intracardiac ultrasound probe, and a proximal end of the ultrasound catheter is connected to the control handle, wherein the ultrasound catheter encloses the flexible circuit board unit and a multi-core coaxial cable, wherein the multi-core coaxial cable goes through the control handle to connect to the intermediate connector, and wherein the intermediate connector is configured to connect to a system end.

17. An intracardiac ultrasound catheter system, comprising the intracardiac ultrasound probe according to claim 3, an ultrasound catheter, a control handle, and an intermediate connector, wherein a distal end of the ultrasound catheter is connected to the intracardiac ultrasound probe, and a proximal end of the ultrasound catheter is connected to the control handle, wherein the ultrasound catheter encloses the flexible circuit board unit and a multi-core coaxial cable, wherein the multi-core coaxial cable goes through the control handle to connect to the intermediate connector, and wherein the intermediate connector is configured to connect to a system end.

18. The intracardiac ultrasound catheter system according to claim 16, wherein the signal wires of the multi-core coaxial cable first pass through a magnetic ring to be soldered on the intermediate connector, and wherein the intermediate connector is plugged into the system end.

19. The intracardiac ultrasound catheter system according to claim 18, wherein both front and back sides of a circuit board of the intermediate connector are provided with metal shielding covers.

* * * * *